(12) United States Patent
Niremberg

(10) Patent No.: US 11,304,675 B2
(45) Date of Patent: Apr. 19, 2022

(54) BREAST PHANTOM WITH ENCAPSULATED HYDROGEL

(71) Applicant: Hologic, Inc., Marlborough, MA (US)

(72) Inventor: Danielle Niremberg, New York, NY (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 17/023,805

(22) Filed: Sep. 17, 2020

(65) Prior Publication Data
US 2021/0128098 A1    May 6, 2021

Related U.S. Application Data

(60) Provisional application No. 62/930,448, filed on Nov. 4, 2019.

(51) Int. Cl.
*G09B 23/28* (2006.01)
*A61B 6/00* (2006.01)

(52) U.S. Cl.
CPC ............ *A61B 6/583* (2013.01); *G09B 23/286* (2013.01); *A61B 6/502* (2013.01)

(58) Field of Classification Search
CPC ....... G09B 23/286; A61B 6/583; A61B 6/502; A61B 8/587; A61B 5/0093; A61B 5/4244; A61B 5/0035; G01R 33/30; G01R 33/58
See application file for complete search history.

(56) References Cited

U.S. PATENT DOCUMENTS

| | | | |
|---|---|---|---|
| 7,288,759 B2 | 10/2007 | Frangioni et al. | |
| 8,906,268 B2 | 12/2014 | Boutet et al. | |
| 9,920,188 B2 | 3/2018 | Vogt et al. | |
| 2015/0164463 A1* | 6/2015 | Oraevsky | A61B 5/0095 |
| | | | 73/866.4 |

OTHER PUBLICATIONS

2D Versus 3D Cell Cultures, Mimetas Website, https://mimetas.com/article/2d-versus-3d-cell-cultures, 6 pages (Date Printed Dec. 15, 2020).

(Continued)

*Primary Examiner* — Don K Wong
(74) *Attorney, Agent, or Firm* — Merchant & Gould P.C.

(57) ABSTRACT

Methods and devices for testing effects of external stimuli on breast appearance in an x-ray image are provided. A model for testing may include a breast phantom with an encapsulated hydrogel. In some examples, a three-dimensional cell culture and/or microfluidic channels may be encapsulated in the hydrogel. A first set of x-ray images of the model may be captured, thermal energy may be applied to the model, and a second set of x-ray images of the model may be captured while the thermal energy is being applied for comparison with the first set to determine effects of the thermal energy on appearance of the model. By incrementally increasing an amount of thermal energy applied and capturing subsequent x-ray images for comparison, an appropriate temperature range may be determined for heating compression surfaces of a breast imaging system to reduce compression-related pain and discomfort for patients without compromising x-ray image quality.

14 Claims, 8 Drawing Sheets

(56) References Cited

OTHER PUBLICATIONS

Bahram et al., "An Introduction to Hydrogels and Some Recent Applications," Chapter 2 Emerging Concepts in Analysis and Applications of Hydrogels, edited by Sutapa Biswas Majee, 31 pages (Aug. 24, 2016).
Lee et al., "Hydrogels for Tissue Engineering," Chemical Reviews, vol. 101, No. 7, pp. 1869-1879 (Jul. 2001).
Marco Caballo et al., "Patient-based 4D digital breast phantom for perfusion contrast-enhanced breast CT imaging," Med. Phys., vol. 45, No. 10, pp. 4448-4460 (Oct. 2018).
MTOAC: Multi-compartmental Tumor-on-a-chip Device to Mimic the Tumor Microenvironment Breast Cancer, Elveflow Plug & Play Microfluidics Website, https://www.elveflow.com/microfluidic-innovation-center/microfluidics-research-projects/organ-chip-multi-compartmental-tumor-chip-study-breast-cancer-mtoac-project.
Relieving Pain Without Medication, Harbor Light Hospice Website, https://www.harborlighthospice.com/resources/pain-management/relieving-pain-without-medication/, 8 pages (Copyright 2020).
Seliktar, "Designing Cell-Compatible Hydrogels for Biomedical Applications," Science, vol. 336, pp. 1124-1128 (Jun. 1, 2012).
Serbo et al., "Vascular tissue engineering: biodegradable scaffold platforms to promote angiogenesis," Stem Cell Research & Therapy, vol. 4, No. 8, 8 pages (2013).
Tibbitt et al., "Hydrogels as Extracellular Matrix Mimics for 3D Cell Culture," Biotechnology and Bioengineering, vol. 103, No. 4, pp. 655-663 (Jul. 1, 2009).
Ustyugov et al., "Development of 3D Cell Culture on Ultra-High Molecular Weight Polyethylene (UHMWPE) as the Basis of Cellular Matrix," Biomedical Chemistry: Research and Methods, vol. 1, No. 8, 3 pages (2018).
Vantangoli et al., "MCF-7 Human Breast Cancer Cells Form Differentiated Microtissues in Scaffold-Free Hydrogels," PLoS One, vol. 10, No. 8, 20 pages (Aug. 12, 2015).
Wang et al., "Shear Forces from Flow Are Responsible for a Distinct Statistical Signature of Adherent Microbubbles in Large Vessels," Mol. Imaging, vol. 12, No. 6, pp. 396-408 (Sep. 1, 2013).
What are Imaging Phantoms?, National Institute of Standards and Technology Website, https://www.nist.gov/topics/physics/what-are-imaging-phantoms, 8 pages (Updated Sep. 29, 2020).
Zhou et al., "In Vitro Regeneration of Patient-specific Ear-shaped Cartilage and Its First Clinical Application for Auricular Reconstruction," EBioMedicine, vol. 28, pp. 287-302 (2018).

\* cited by examiner

BREAST PHANTOM WITH ENCAPSULATED HYDROGEL

CROSS-REFERENCE TO RELATED APPLICATION

This application claims priority to U.S. Provisional Patent Application No. 62/930,448, filed on Nov. 4, 2019, entitled "BREAST PHANTOM WITH ENCAPSULATED HYDROGEL," which is incorporated herein by reference in its entirety.

BACKGROUND

Breast imaging processes, including mammography, tomosynthesis, and computed tomography, capture x-ray images of the breasts to screen for breast cancer. The breast imaging processes involve compression of the breast between surfaces of a breast support platform and a compression paddle prior to and during image capture. Compression serves a number of purposes, including to: (1) make the breast thinner in the direction of x-ray flux and thereby reduces patient radiation exposure from the level required to image the thicker parts of a breast that are not compressed; (2) make the breast more uniform in thickness in the direction of x-ray flux and thereby facilitates more uniform exposure at the image plane over the entire breast image; (3) immobilize the breast during the x-ray exposure and thereby reduces image blurring; and (4) bring breast tissues out from the chest wall into the imaging exposure field and thus allows for more tissue imaging.

However, many patients report pain and discomfort caused by the compression of the breast, as well as additional discomfort due to the cold temperature of the surfaces of the breast support platform and compression paddle. The pain and discomfort experienced may potentially cause the patient to move, which negatively impacts image quality. Additionally, the pain and discomfort experienced may deter some patients from being screened, which is of detriment to the patients because of the key role breast imaging processes play in early breast cancer detection.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe an apparatus and method thereof for testing effects of external stimuli, including temperature, on an appearance of a breast in an x-ray image. In one aspect, the technology relates to a method comprising: capturing a first set of x-ray images of a model comprising a breast phantom with an encapsulated hydrogel, applying thermal energy to the model, and capturing a second set of x-ray images of the model while the thermal energy is being applied to enable a comparison of an appearance of the model between the first set and the second set of x-ray images.

In an example, applying the thermal energy to the model comprises applying the thermal energy to one or more of a first compression surface and a second compression surface of a breast imaging system, and compressing the model between the first compression surface and the second compression surface prior to and while capturing the second set of x-ray images, where contact of the model with the first compression surface and/or the second compression surface may transfer the thermal energy to the model. In another example, the first compression surface and/or the second compression surface may be heated to a temperature in a range of about 30° C. to about 45° C.

In another example, a cell culture may be encapsulated in the hydrogel to enable a comparison of an appearance of cells within the cell culture between the first set and the second set of x-ray images. In still another example, the appearance of the cells may be further analyzed using confocal microscopy. In yet another example, a plurality of channels corresponding to a vasculature of the breast may be encapsulated in the hydrogel and fluids may be circulated within the plurality of channels while the first and second set of x-ray images are captured.

In a further example, an amount of the thermal energy applied to the model may be increased, and a third set of x-ray images of the model may be captured while the increased amount of thermal energy is being applied to enable a comparison of the appearance of the model between the second set and the third set of x-ray images.

In another aspect, the technology relates to an apparatus comprising a breast phantom and a hydrogel encapsulated in the breast phantom. In an example, a three-dimensional cell culture may be encapsulated in the hydrogel. In another example, a plurality of channels corresponding to a vasculature of the breast may be encapsulated in the hydrogel, where fluids may be circulated within the plurality of channels.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

Figure 1A:
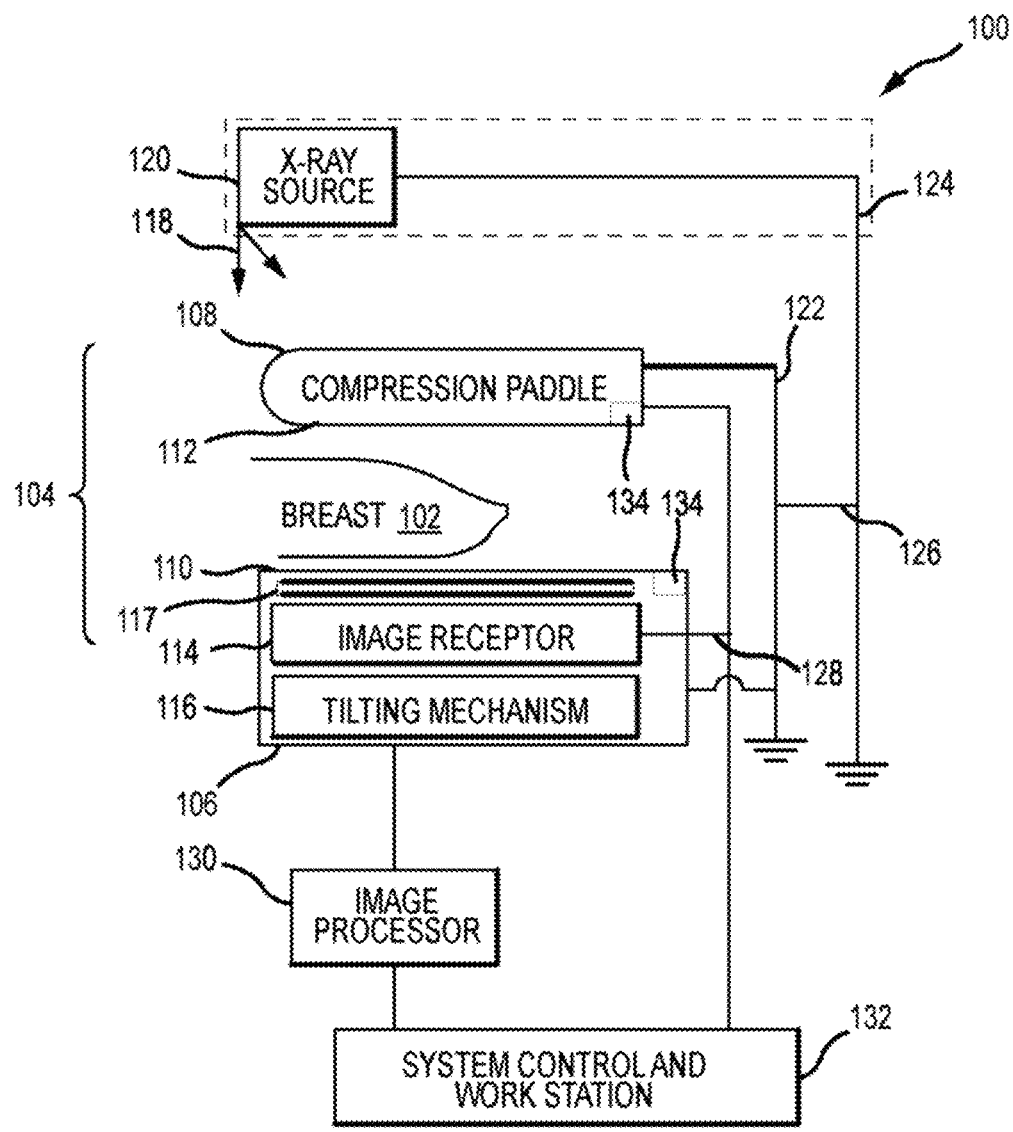
FIG. 1A is a schematic view of an exemplary breast imaging system.

The technologies described herein relate to an apparatus and method thereof for testing effects of external stimuli, including temperature, on an appearance of a breast in an x-ray image. Patients may experience pain or discomfort during breast imaging processes when the breast is compressed, which must be done with sufficient force to immobilize the breast and spread out the breast tissues for x-ray imaging. The pain or discomfort experienced by the patient may be a result of sensory receptor activation. For example, patients may feel pain because of baroreceptor activation created by the build-up of pressure from the breast compression. By activating other sensory receptors, such as thermoreceptors, the perceived pain may be decreased. This can be a result of the same nerve pathways in the body being used to transmit the relevant sensations (heat, pain, and pressure). As an example, skin stimulation by applying a temperature change to the skin may lessen or block a feeling of pain. Some discomfort may also be experienced due to the cold temperature of compression surfaces of breast imaging systems that come into direct contact with the breast when compressed. Applying thermal energy to the compression surfaces in direct contact with the breast when compressed (e.g., by increasing a temperature of the compression surfaces) may transfer the thermal energy to the skin of the breast serving to both activate the thermoreceptors to distract the patients from the compression pain, as well as reduce temperature-related discomfort experienced by patients.

However, one concern of skin stimulation by applying a temperature change is the effects of a cholinergic response on image quality. As temperature increases, for example, a cholinergic response may occur causing smooth muscles to contract and blood vessels to dilate. Vasodilation within the breast affects blood flow and blood is radiopaque, which may alter an appearance of the breast in the x-ray image. Therefore, it is important to test how the application of thermal energy affects the breast appearance in the x-ray image using a physiologically responsive model of the breast in order to determine an appropriate temperature range for heating the compression surfaces to reduce pain and discomfort for patients without compromising the quality of the x-ray images captured. The physiologically responsive model may limit the need for performing clinical studies to test effects of the application of thermal energy, as well as other stimuli or future considerations for enhancements to the breast imaging system, on breast appearance in the x-ray images.

A breast phantom that includes at least one encapsulated hydrogel is an example model that may be used for testing. For example, a first set of x-ray images of the model may be captured, thermal energy may be applied to the model, and a second set of x-ray images of the model may be captured while the thermal energy is being applied. The first and second set of x-ray images may be compared to determine whether and how the applied thermal energy affects the appearance of the model in an x-ray image to inform how the application of thermal energy may affect the appearance of an actual breast in an x-ray image. For example, the comparison of the model's appearance from the first set of x-ray images to the second set of x-ray images may include a comparison to identify physical changes to a structure of the model and/or changes induced by the model's response to the applied thermal energy. As one example, changes in the radiopacity of the model from the first set of x-ray images to the second set of x-ray images may be determined, the increase in radiopacity caused by the increased blood flow from vasodilation in response to the applied thermal energy. As another example, changes to an appearance of cells (e.g., a group or a mass of cells) within the hydrogel of the model from the first set of x-ray images to the second set of x-ray images may be determined. In some examples, the determination may be made by a radiologist, or other similarly qualified specialist. In other examples, artificial intelligence may be employed for the determination. For example, the artificial intelligence may utilize image recognition techniques to determine differences in appearance. By incrementally increasing an amount of thermal energy applied and capturing subsequent x-ray images for comparison, an appropriate temperature range may be determined for heating the compression surfaces to reduce pain and discomfort for patients without compromising the quality of the x-ray images captured.

In describing examples illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Figure 1B:
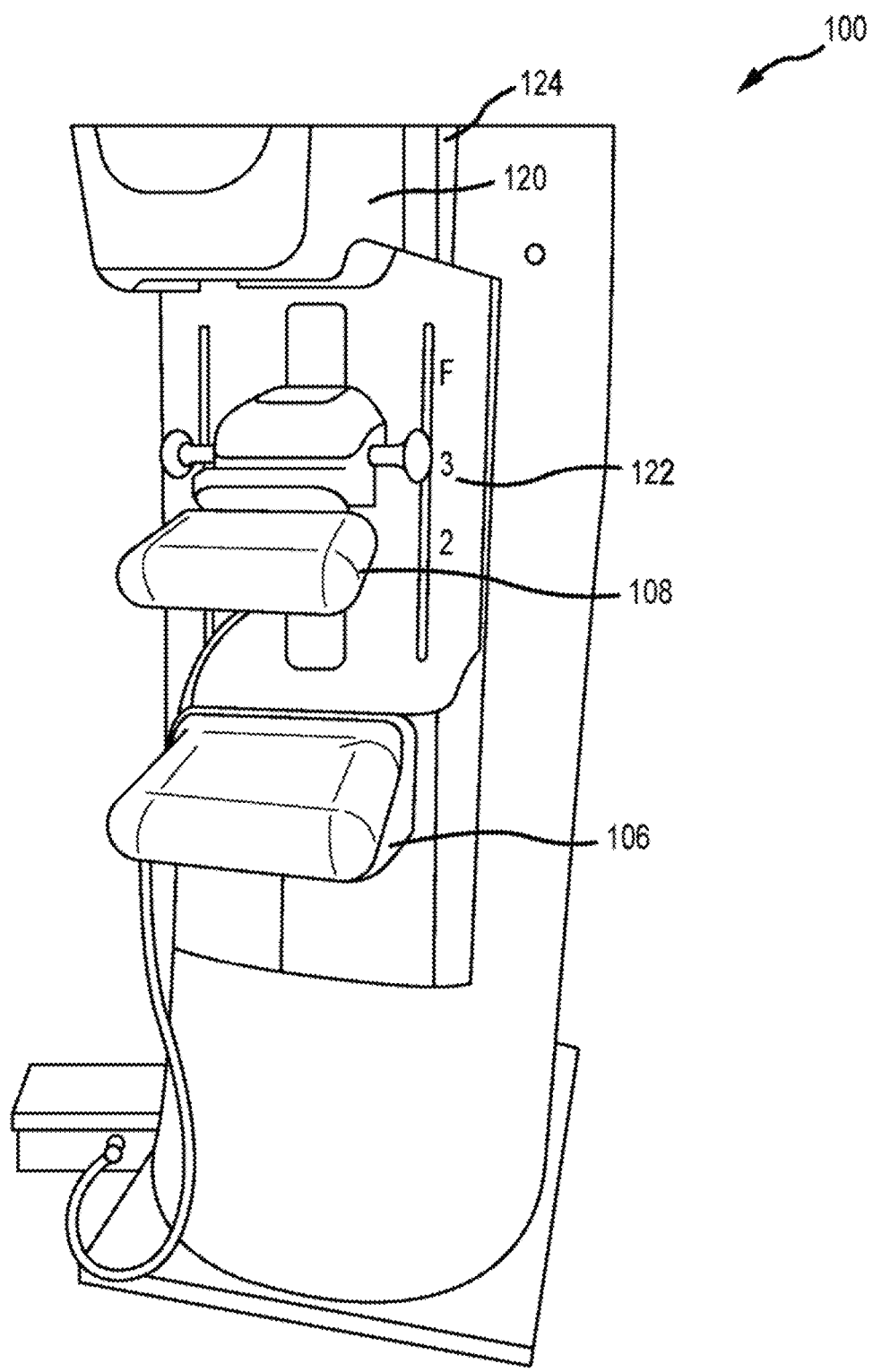
FIG. 1B is a perspective view of the breast imaging system of FIG. 1A.

FIG. 1A is a schematic view of an exemplary breast imaging system 100. FIG. 1B is a perspective view of the breast imaging system 100. Referring concurrently to FIGS. 1A and 1B, the breast imaging system 100 is configured to immobilize a patient's breast 102 for x-ray imaging (one or more of a mammography mode, a tomosynthesis mode, and a computed tomography (CT) mode) via a breast compression immobilizer unit or compression system 104. In the example, the compression system 104 includes a breast support platform 106 and a moveable compression paddle 108. The breast support platform 106 and the compression paddle 108 each have a compression surface 110 and 112, respectively, with the compression surface 112 configured to move towards the support platform 106 to compress and immobilize the breast 102. In known systems, the compression surfaces 110, 112 are exposed so as to directly contact the breast 102. The support platform 106 also houses an image receptor 114 and, optionally, a tilting mechanism 116. In some examples, the support platform 106 also houses an anti-scatter grid 117. The compression system 104 is in a path of an imaging x-ray beam 118 emanating from an x-ray source 120, such that the beam 118 impinges on the image receptor 114.

The compression system 104 is supported on a first support arm 122 and the x-ray source 120 is supported on a second support arm, also referred to as a tube arm 124. For mammography, support arms 122 and 124 can rotate as a unit about an axis 126 between different imaging orientations such as cranial-caudal (CC) and mediolateral oblique (MLO) views, so that the breast imaging system 100 can take a mammogram projection image at each orientation. In operation, the image receptor 114 remains in place relative to the support platform 106 while an image is taken. The compression system 104 releases the breast 102 for movement of support arms 122, 124 to a different imaging orientation. For tomosynthesis, the support arm 122 stays in place, with the breast 102 immobilized and remaining in place, while at least the tube arm 124 rotates the x-ray source 120 relative to the compression system 104 and the compressed breast 102 about the axis 126. The breast imaging system 100 takes plural tomosynthesis projection images of the breast 102 at respective angles of the x-ray beam 118 relative to the breast 102. As such, the compression system 104 and tube arm 124 may be rotated discrete from each other, unless matched rotation is required or desired for an imaging procedure.

In some examples, the anti-scatter grid 117 is positioned between the compression surface 110 and the image receptor 114 and is configured to reduce x-rays scattered by the breast tissue from reaching the image receptor 114 during mammography and/or tomosynthesis x-ray imaging. The anti-scatter grid 117 may include a plurality of septa formed from a radio-opaque material or a highly x-ray absorbing material, such as lead, and separated by interspaces that are formed from a radiolucent material or a low-x-ray attenuating material, such as carbon fiber or aluminum. In operation, the anti-scatter grid 117 moves relative to the image receptor 114 to reduce moire patterns in the resulting images. The anti-scatter grid 117 may also retract away from the image receptor 114 as required or desired.

Concurrently and optionally, the image receptor 114 may be tilted relative to the breast support platform 106 and coordinated with the rotation of the second support arm 124. The tilting can be through the same angle as the rotation of the x-ray source 120, but may also be through a different angle selected such that the x-ray beam 118 remains substantially in the same position on the image receptor 114 for each of the plural images. The tilting can be about an axis 128, which can but need not be in the image plane of the image receptor 114. The tilting mechanism 116 that is coupled to the image receptor 114 can drive the image receptor 114 in a tilting motion. In some examples, the anti-scatter grid 117 may be coupled to the image receptor 114 such that the anti-scatter grid 117 tilts with the image receptor 114. In other examples, the anti-scatter grid 117 may not tilt with the image receptor 114 and be independent therefrom.

For tomosynthesis imaging and/or CT imaging, the breast support platform 106 can be horizontal or can be at an angle to the horizontal, e.g., at an orientation similar to that for conventional MLO imaging in mammography. The breast imaging system 100 can be solely a mammography system, solely a CT system, or solely a tomosynthesis system, or a "combo" system that can perform multiple forms of imaging.

When the system is operated, the image receptor 114 produces imaging information in response to illumination by the imaging x-ray beam 118, and supplies it to an image processor 130 for processing and generating breast x-ray images. A system control and work station unit 132 including software controls the operation of the system and interacts with the operator to receive commands and deliver information including processed-ray images.

One challenge with the breast imaging system 100 is how to efficiently immobilize and compress the breast 102 for the desired or required imaging. A health professional, typically an x-ray technologist, generally positions and adjusts the breast 102 between the support platform 106 and the compression paddle 108 while pulling tissue towards the imaging area to immobilize the breast 102 and keep it in place, with as much of the breast tissue as practicable being between the compression surfaces 110, 112. Because the breast imaging system 100 is typically disposed within a patient room that is relatively cold so as to facilitate imaging system operation, the outer surfaces of the breast imaging system 100, for example, the compression surfaces 110, 112 are generally cold to the touch. When the support platform 106 and/or the compression paddle 108 are cold, the patient may experience discomfort and anxiety, which may result in movement and an improperly positioned breast. This even sometimes requires an x-ray image to be re-taken, which delivers unnecessary x-ray doses to the patient. In addition to the discomfort experienced due to the cold support platform 106 and/or the compression paddle, the compression of the 102 breast between the compression surfaces 110, 112 may in general be painful for the patient causing further anxiety. For example, the pain may be a result of baroreceptor activation due to build-up of pressure from the breast compression and/or nociceptor activation.

Accordingly, a heating system 134 can be coupled to the support platform 106, the compression paddle 108, or both the support platform 106 and the compression paddle 108 to generate heat and increase the temperature of one or both of the compression surfaces 110, 112 to reduce patient pain and discomfort. In some examples, a temperature of both the compression surfaces 110, 112 may be increased to at least a similar if not the same temperature to prevent a temperature gap between the compression surfaces 110, 112 that could cause further discomfort as only some portions of the breast 102 may be warm while other portions remain cold.

In one example, to generate heat, the heating system 134 may induce an electric current flow across a transparent conducting film coupled to an inner surface of a housing of the breast support platform 106 and/or compression paddle 108. In another example, the transparent conducting film may be adjacent to at least a portion of the compression paddle 108 and a front wall of a housing of the breast support platform 106, and inducing the electric current flow may include independently controlling the current applied to the transparent conducting film at the compression paddle 108 and the current applied to the transparent conducting film at the front wall. In still another example, a flow of air may be heated and blown across an inner surface of the housing of the breast support platform 106 and/or compression paddle 108.

The typical temperature of the outer surfaces of an unheated breast imaging system 100 may be in a range of about 18° C. to about 21° C., while the heating system 134 may be configured to raise that temperature to a range of about 30° C. to about 35° C. or higher. In addition to the reducing temperature-related patient discomfort, skin stimulation resulting from the contact of the breast 102 with the heated compression surfaces 110, 112 may activate thermoreceptors that may lessen or block the patient's perceived pain due to the build-up of pressure from the breast compression. Therefore, increasing the temperature of the compression surfaces 110, 112 may serve to both activate the thermoreceptors to distract the patients from the compression pain, as well as reduce the temperature-related discomfort experienced by patients during the breast imaging process.

However, one concern of skin stimulation by applying heat is the effects of a cholinergic response on image quality. A cholinergic response causes smooth muscles to contract and blood vessels to dilate. The dilation of blood vessels within the breast 102 affects blood flow and blood is radiopaque, which may alter an appearance of the breast 102 in the x-ray image. For example, radiopaque substances, such as blood, block radiation and thus appear white on an x-ray image. Therefore, it is important to test how the application of heat affects an appearance of the breast 102 in the x-ray image using an accurate model of the breast 102 in order to determine an appropriate temperature range for heating the compression surfaces 110, 112 to reduce pain and discomfort for the patient without compromising the quality of the x-ray images. A breast phantom that includes at least one encapsulated hydrogel is one example model, described in detail in FIG. 2 below. A breast phantom is a structure that anatomically mimics breast tissue. Breast phantoms are often used to test a quality and repeatability of an imaging apparatus, such as the breast imaging system 100. Although, breast phantoms are anatomically relevant, they do not mimic a physiological response of the breast. Therefore, effects of stimuli, such as heat, are not easily noticeable. By including the at least one encapsulated hydrogel within the breast phantom, both an anatomically relevant and physiologically responsive model of the breast is created.

A similar model may be used to test effects of various different types of electrical and mechanical stimuli on an appearance of the breast 102 within an x-ray image. However, for clarify, the effects of heat or temperature changes on the appearance of the breast 102 in an x-ray image are described herein.

Figure 2:
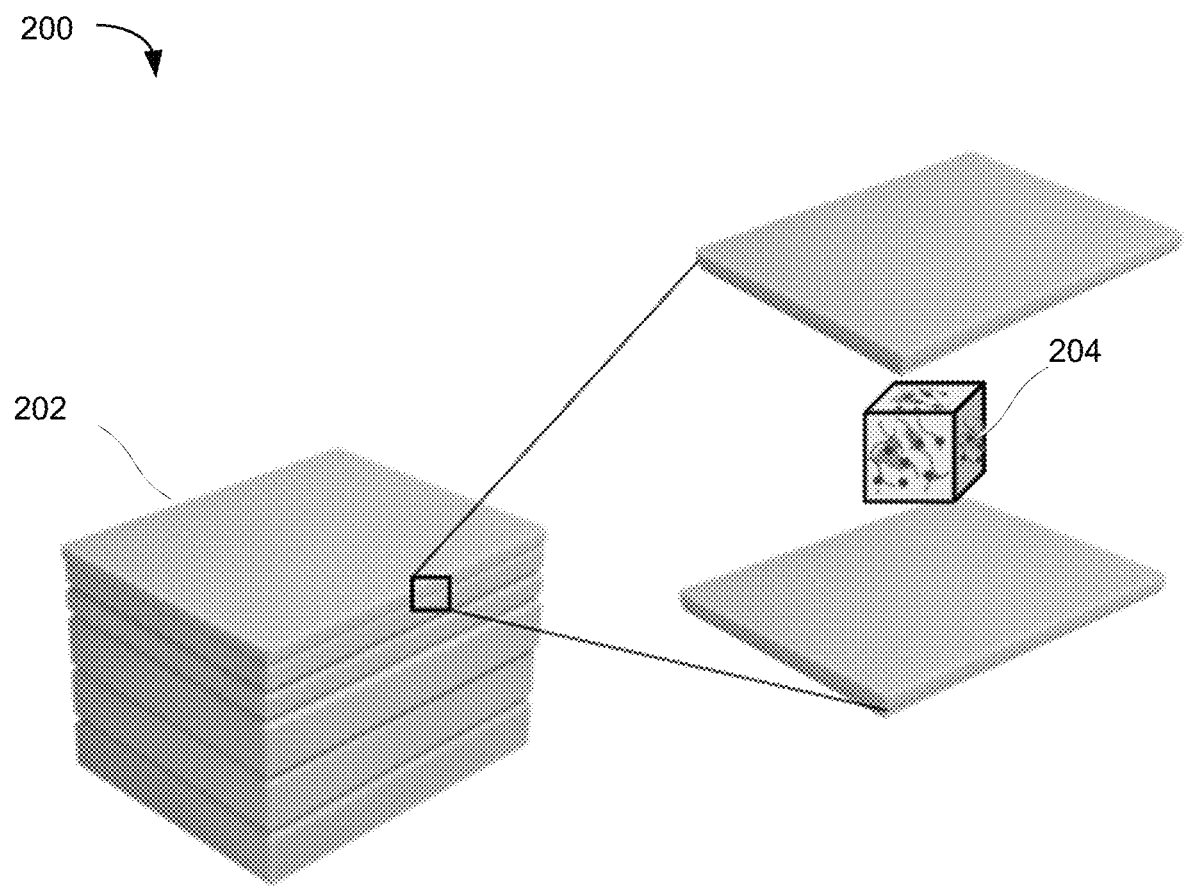
FIG. 2 is an example model for testing effects of stimuli on breast appearance in an x-ray image.

FIG. 2 is an example model 200 for testing effects of stimuli on breast appearance in an x-ray image. One example stimuli may include heat. For example, a first set of x-ray images of the model 200 may be captured, thermal energy may be applied to the model 200, and a second set of x-ray images of the model 200 may be captured while the thermal energy is being applied. The first and second set of x-ray images may be compared to determine whether and how the applied thermal energy affects the appearance of the model 200 in an x-ray image to inform how the application of thermal energy may affect the appearance of an actual breast in an x-ray image. In some examples, the determination may be made by a radiologist, or other similarly qualified specialist. In other examples, artificial intelligence may be employed for the determination. For example, the artificial intelligence may utilize image recognition techniques to determine differences in appearance.

The model 200 may include a breast phantom 202 with at least one encapsulated hydrogel 204. The breast phantom 202 may provide an anatomically relevant model of the breast. For example, the breast phantom 202 may include a plurality of slabs that are at least partially manufactured from breast-equivalent material (e.g., substitute material for breast tissue). In some examples, the breast-equivalent material may comprise a 50/50 ratio of gland and adipose tissue (e.g., BR50/50).

The hydrogel 204 comprises a network of hydrophilic polymer chains that may be prepared from one or more monomers, an initiator, and a cross-linker employing one or more of chemical crosslinking, physical crosslinking, free radical polymerization, and irradiation crosslinking. In some examples, the hydrogel may be comprised of natural materials. In other examples, the hydrogel may be comprised of synthetic materials. A type of crosslinking or polymerization performed may be based on the type of materials selected. The materials may be selected based on factors associated with an anatomy of the breast to be modeled to simulate different clinical scenarios. As one example, if a dense breast is to be modeled particular types of materials may be selected to more accurately represent the dense breast tissue. As additional examples, a breast with lesions or scar tissue may be modeled, or different stages of breast cancer may be modeled.

In some examples, the hydrogel 204 may be prepared as a chip or other similar device for insertion into the breast phantom 202. For example, the hydrogel 204 may be inserted into an interior portion of the breast phantom 202 such that when the hydrogel 204 is inserted, the hydrogel 204 is surrounded by or encased within the breast phantom 202, while still allowing the hydrogel 204 to be easily removed. In some examples, the hydrogel 204 may be inserted between two of the plurality of slabs, as illustrated. In additional examples, more than one hydrogel 204 may be inserted into the breast phantom 202 to form the model 200.

For example, a plurality of hydrogels 204 can be positioned throughout the interior of the breast phantom 202.

The hydrogel 204 may mimic a microenvironment of a breast, supporting cell growth. Accordingly, in some examples, a cell culture may be encapsulated in the hydrogel 204, the hydrogel 204 serving as a three-dimensional (3D) scaffold. The cell culture may include a variety of cells that may be naturally present in breast tissue, as described in greater detail with respect to FIG. 3. X-ray images captured prior to and following the application of thermal energy to the model 200 may be compared to determine whether and how the appearance of the cells in the x-ray images are collectively affected by the application of the thermal energy. The determination may inform how application of thermal energy may affect the appearance of cells or tumor masses in an actual breast in an x-ray image, and thus the ability of radiologists to identify certain suspicious groups of cells, among other examples. In additional examples, the hydrogel 204 may be removed from the breast phantom 202 following application of the thermal energy and analyzed further using confocal microscopy (e.g., z-stack imaging). For example, confocal microscopy may allow analysis of the appearance of cells on an individual level.

In further examples, a plurality of channels may also be encapsulated in the hydrogel 204. As described in greater detail with respect to FIG. 4 below, the channels may be microfluidic channels that correspond to a vasculature of the breast (e.g., blood vessels of the breast). Fluids may be circulated through the channels to mimic a flow of blood within the vasculature of the breast. For example, the fluid may be radiopaque fluid for modeling the blood. The x-ray images captured prior to and following the application of thermal energy to the model 200 may be compared to determine whether and how increases in fluid flow caused by the application of thermal energy affect the appearance of the model 200 in the x-ray images. The determination may inform how increased blood flow from dilation of blood vessels (e.g., resulting from cholinergic response caused by the application of thermal energy) may affect the appearance of an actual breast in an x-ray image. Additionally, modeling the vasculature of the breast and determining effects of blood flow on breast appearance is important because when cancer cells or tumors are present at a site in the breast, there may be increased blood flow to the site to feed those cells. Therefore, cancer cells and tumors are more susceptible to being affected by changes in breast appearance due to blood flow changes.

In addition to implementing the model 200 to test the effects of stimuli, such as heat, on breast appearance in an x-ray image, the model 200 may be used to test contrast imaging of a breast to determine an optimal contrast agent, an optimal dosage of contrast agent, and an optimal image acquisition time, among other similar factors, in different clinical scenarios. Testing of contrast imaging is difficult and typically requires a human subject for testing. The model 200 provides a simpler and effective method for testing. For example, the fluid circulated through the plurality of channels encapsulated in the hydrogel 204 may be a contrast agent to mimic a flow of contrast agent within the vasculature of the breast during contrast imaging. In some examples, different types of contrast agents may be administered to the model 200, and x-ray images of the model 200 may be captured and analyzed to determine an optimal contrast agent in a particular clinical scenario (e.g., a patient with dense breasts, a patient having blocked vasculature, or a patient having breast cancer). In other examples, different dosages of the contrast agent may be administered and x-ray images may be captured of the model 200 at each dosage to determine an optimal contrast dose to administer in a particular clinical scenario. In further examples, x-ray images of the model 200 captured over time following administration of the contrast agent may be analyzed to determine an optimal image acquisition time in a particular clinical scenario. As previously discussed, the materials of the hydrogel 204 may be selected based on factors associated with an anatomy of the breast to be modeled to simulate different clinical scenarios. Therefore, the model 200 may be altered for each of the different clinical scenarios (e.g., by preparing a new hydrogel 204 to mimic the respective clinical scenario), and one or more of the optimal contrast agent, the optimal dose, and the optimal image acquisition time may be determined for each clinical scenario.

Figure 3:
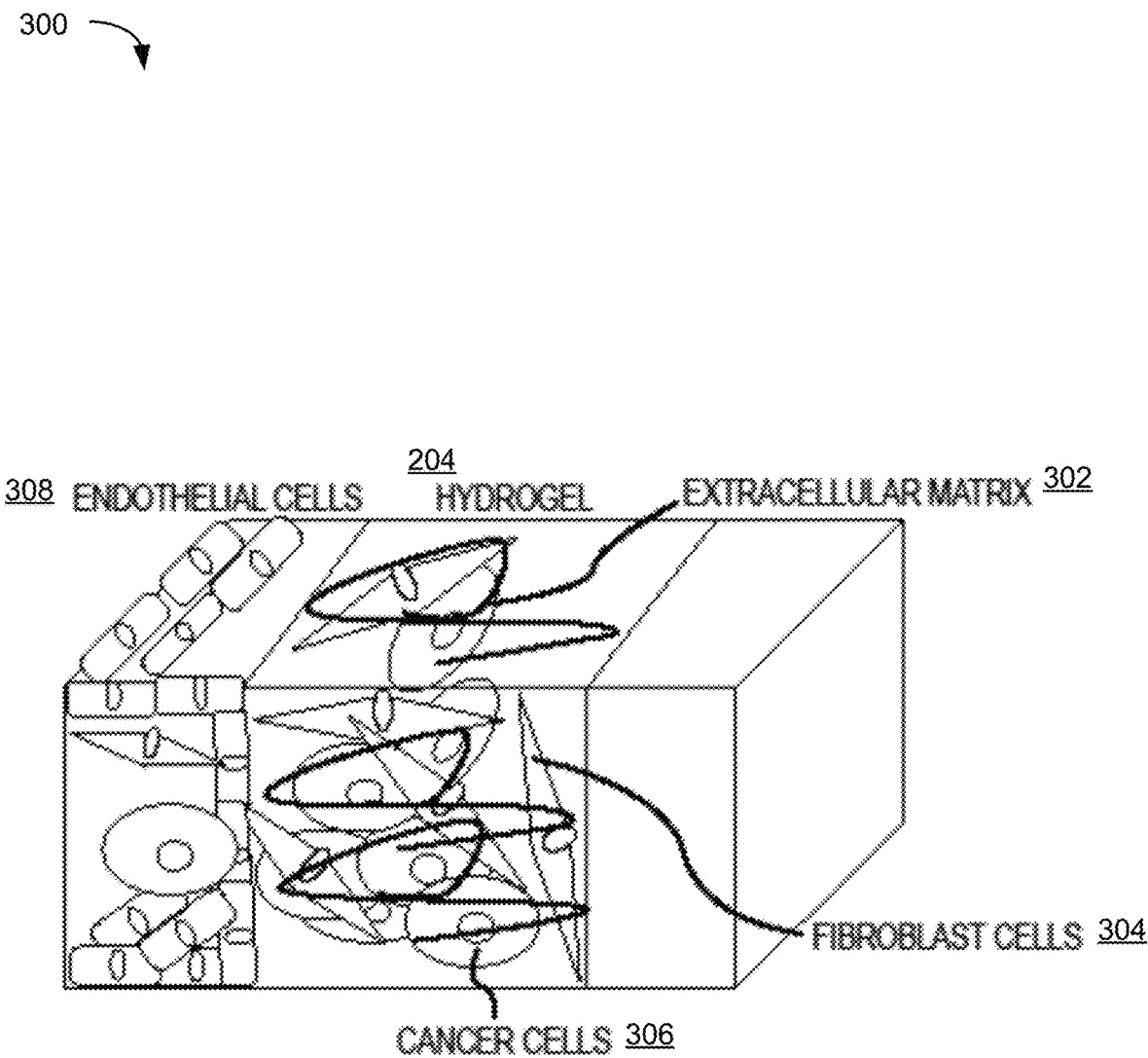
FIG. 3 is a diagram depicting an example three-dimensional cell culture encapsulated in a hydrogel.

FIG. 3 is a diagram 300 depicting an example cell culture encapsulated in the hydrogel 204. The hydrogel 204 may mimic a microenvironment of the breast, comprising an extracellular matrix 302 supporting the cell culture. The cell culture includes a variety of cells that may be naturally present in breast tissue. Example cells include breast fibroblast cells 304, breast cancer cells 306, and breast endothelial cells 308. In some examples, a large number of breast cancer cells 306 may be seeded to create a tumor detectable by x-ray image.

As previously described with respect to FIG. 2, in some examples, the hydrogel 204 may be prepared as a chip or other similar device inserted into an interior portion of the breast phantom 202 such that when the hydrogel 204 is inserted, the hydrogel 204 is surrounded by or encased within the breast phantom 202, while still allowing the hydrogel 204 to be easily removed. Therefore, unless x-ray images of the model 200 are being captured, the hydrogel 204 may be independent from the breast phantom 202 and remain in an incubator, for example, to grow and maintain the cell culture. As such, additional cells or other necessary factors for cell growth may be added at any time. Additionally, the ability of the hydrogel 204 to be inserted and removed from the breast phantom 202 may be cost effective. For example, once a hydrogel 204 is no longer usable (e.g., due to overcrowding of cells within the cell culture), only the hydrogel 204 needs to be disposed of and another similar hydrogel created, while the breast phantom 202 may be reusable for insertion of the newly created hydrogel.

To test the effects of stimuli, such as heat, on breast appearance in an x-ray image, the hydrogel 204 may be inserted into the breast phantom 202 (e.g., collectively the model 200) and a first set of x-ray images may be captured of the model 200 by breast imaging system 100. The first set of x-ray images may serve as a control to determine an appearance of the model 200 before any thermal energy is applied. Thermal energy may then be applied to the model 200. For example, one or both of the compression surfaces 110, 112 of the breast imaging system 100 may be heated by the heating system 134 to increase a temperature of the one or both compression surfaces 110, 112. The compression surfaces 110, 112 may be heated while the model 200 is removed from the breast imaging system 100 to more realistically represent a clinical setting in which one or both of the compression surfaces 110, 112 would constantly remain heated to a particular temperature throughout the day to maintain thermal stabilization. The thermal energy created by increase in temperature may then be transferred to the model 200 upon contact with one or both compression surfaces 110, 112. A second set of x-ray images may be captured of the model 200 by breast imaging system 100 while the thermal energy is being applied.

The first set of x-ray images and the second set of x-ray images may be compared to determine whether and how an appearance of the model 200 changes when the thermal energy is applied. Specifically, the comparison may determine whether and how an appearance of the cells within the cell culture encapsulated in the hydrogel (particularly the breast cancer cells 306) in the x-ray images are collectively affected by the application of the thermal energy. The determination may inform how application of thermal energy may affect the appearance of cells in an actual breast in an x-ray image. For example, where a large number of breast cancer cells 306 are seeded in the cell culture to create a tumor detectable by x-ray image, the appearance of the tumor may be analyzed as changes to the appearance may affect an ability of radiologists to identify the tumor within the x-ray image.

In additional examples, the hydrogel 204 may be removed from the breast phantom 202 following application of the thermal energy and analyzed further using confocal microscopy (e.g., z-stack imaging). For example, confocal microscopy may allow analysis of the appearance of cells individually. In further examples, various assays may be performed to analyze different features of the cells (e.g., to determine whether a cell is alive or dead, or is actively proliferating, among other examples).

In some examples, the testing process may continue by increasing an amount of the thermal energy applied to the model 200 incrementally and capturing up to an $n^{th}$ set of x-ray images while the increased amount of thermal energy is being applied. In some examples, the testing process may continue until a determination is made that the appearance of the model 200 has changed in the most recently captured set of x-ray images. From this testing process, an appropriate temperature range may be determined for heating the compression surfaces 110, 112 to reduce pain and discomfort for patients without compromising the quality of the x-ray image captured.

Figure 4:
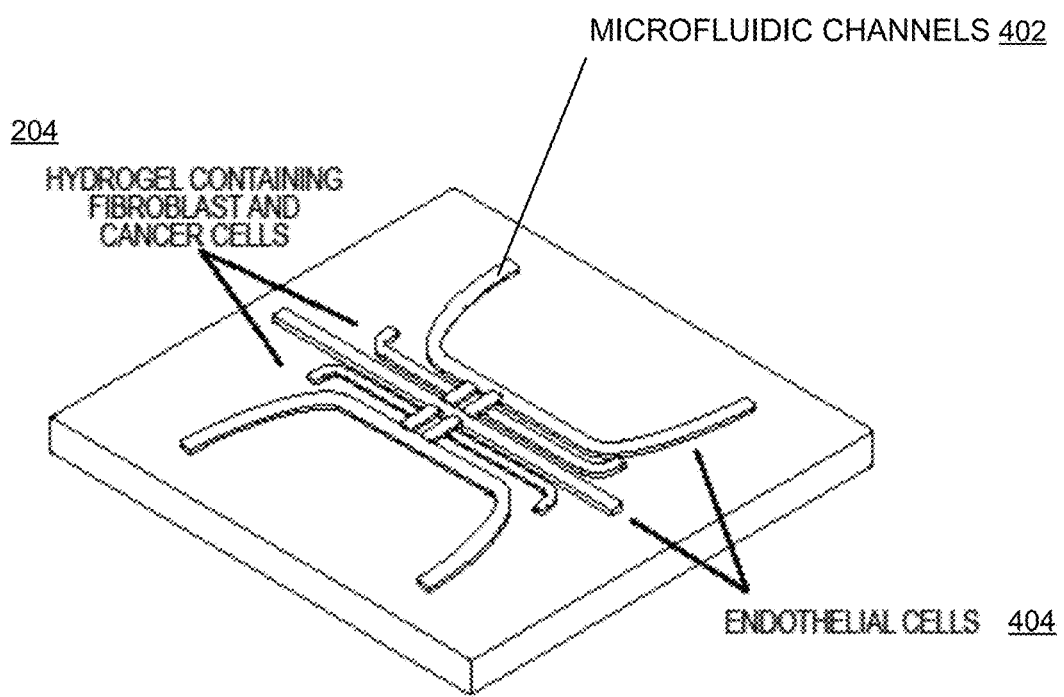
FIG. 4 is a diagram depicting example microfluidic channels encapsulated in a hydrogel.

FIG. 4 is a diagram 400 depicting example microfluidic channels 402 encapsulated in the hydrogel 204. Alternatively, or in addition to the cell culture described with respect to FIG. 3, one or more microfluidic channels 402 that correspond to at least a portion of a vasculature (e.g., blood vessels) of the breast may be encapsulated in the hydrogel 204.

As one simple example, to create a microfluidic channel 402, a needle having a diameter corresponding to a diameter of a breast blood vessel may be inserted into a liquid precursor solution for the hydrogel 204, gel formation may then occur with the needle in place to form the hydrogel 204, and the needle may then be removed to create the microfluidic channel 402. In some examples, endothelial cells 404 may then be seeded along the inner portions of the microfluidic channels 402 to more accurately represent the vasculature of the breast as endothelial cells line an interior surface of blood vessels forming an interface between circulating blood in the lumen and the rest of the vessel. Other processes for creating the microfluidic channels 402 known to those skilled in the art may alternatively be implemented.

Based on a parameter to be tested, the microfluidic channels 402 encapsulated within the hydrogel 204 may vary. For example, to determine how effects of thermal energy application on breast appearance in an x-ray image may differ when one or more blood vessels of the breast are clogged, the microfluidic channels 402 encapsulated in the hydrogel can be altered to simulate the one or more clogged blood vessels.

In some examples, fluids may be circulated through the microfluidic channels 402 to model a flow of blood within the vasculature of the breast 102. For example, because blood is radiopaque, radiopaque fluids may be circulated through the microfluidic channels 402. One example radiopaque fluid used to model blood may include diluted betadine. Additionally, based on the composition of the hydrogel 204, the hydrogel 204 may swell. The ability of the hydrogel to swell may be beneficial to modeling the dynamic nature of vasculature, as opposed to having a static structure. For example, when thermal energy is applied to the model 200 (e.g., the breast phantom 202 with the hydrogel 204 inserted), the microfluidic channels 402 encapsulated in the hydrogel 204 may expand in diameter mimicking dilation of blood vessels in the breast 102. Accordingly, the amount of fluid flowing through the microfluidic channels 402 may increase. Therefore, the microfluidic channels 402 may provide an accurate way to test effects of a cholinergic response resulting from skin stimulation by applying a temperature change (e.g., heat) on x-ray image quality.

For example, to test the effects of heat on breast appearance in an x-ray image, the hydrogel 204 may be inserted into the breast phantom 202 (e.g., collectively the model 200) and a first set of x-ray images may be captured of the model 200 by breast imaging system 100. The fluid may be circulated through the microfluidic channels 402 while the first set of x-ray images are being captured. The first set of x-ray images may serve as a control to determine an appearance of the model 200 before any thermal energy is applied. Thermal energy may then be applied to the model 200. For example, one or both of the compression surfaces 110, 112 of the breast imaging system 100 may be heated by heating system 134 to increase a temperature of the one or both compression surfaces 110, 112. The compression surfaces 110, 112 may be heated while the model 200 is removed from the breast imaging system 100 to more realistically represent a clinical setting in which one or both of the compression surfaces 110, 112 would constantly remain heated to a particular temperature throughout the day. The thermal energy created by increase in temperature may then be transferred to the model 200 upon contact with one or both compression surfaces 110, 112. A second set of x-ray images may be captured of the model 200 by breast imaging system 100 while the thermal energy is being applied and fluids are being circulated within the microfluidic channel 402.

The first set of x-ray images and the second set of x-ray images may be compared to determine whether and how an appearance of the model 200 changes when the thermal energy is applied. Specifically, the comparison may determine whether and how the increase in the amount of radiopaque fluids flowing through the microfluidic channels 402 caused by the application of thermal energy affects an appearance of the model 200 in the x-ray images. The determination may inform how increased blood flow from dilation of blood vessels (e.g., resulting from cholinergic response caused by the application of thermal energy) may affect the appearance of an actual breast in an x-ray image. Additionally, if the cell culture is encapsulated in the hydrogel 204 and includes cancer cells 306, as described in FIG. 3, the determination may inform how the appearance of cancer cells in an actual breast may be affected. For example, when cancer cells are present at a site in the breast, there may be increased blood flow to the site to feed those cells. Therefore, cancer cells may be more susceptible to being affected by changes in breast appearance due to blood flow changes.

In some examples, the testing process may continue by increasing an amount of the thermal energy applied to the model 200 incrementally and capturing up to an $n^{th}$ set of x-ray images while the increased amount of thermal energy is being applied. In some examples, the testing process may continue until a determination is made that the appearance of the model 200 has changed in the most recently captured set of x-ray images. From this testing process, an appropriate temperature range may be determined for heating the compression surfaces 110, 112 to reduce pain and discomfort for patients without compromising the quality of the x-ray image captured.

In other examples, the fluids circulated through the microfluidic channels may be contrast agents for modeling contrast imaging to help inform optimal contrast dose to administer, optimal image acquisition time, as well as an optimal agent based on the density of the patient's breast, among other examples.

Figure 5:
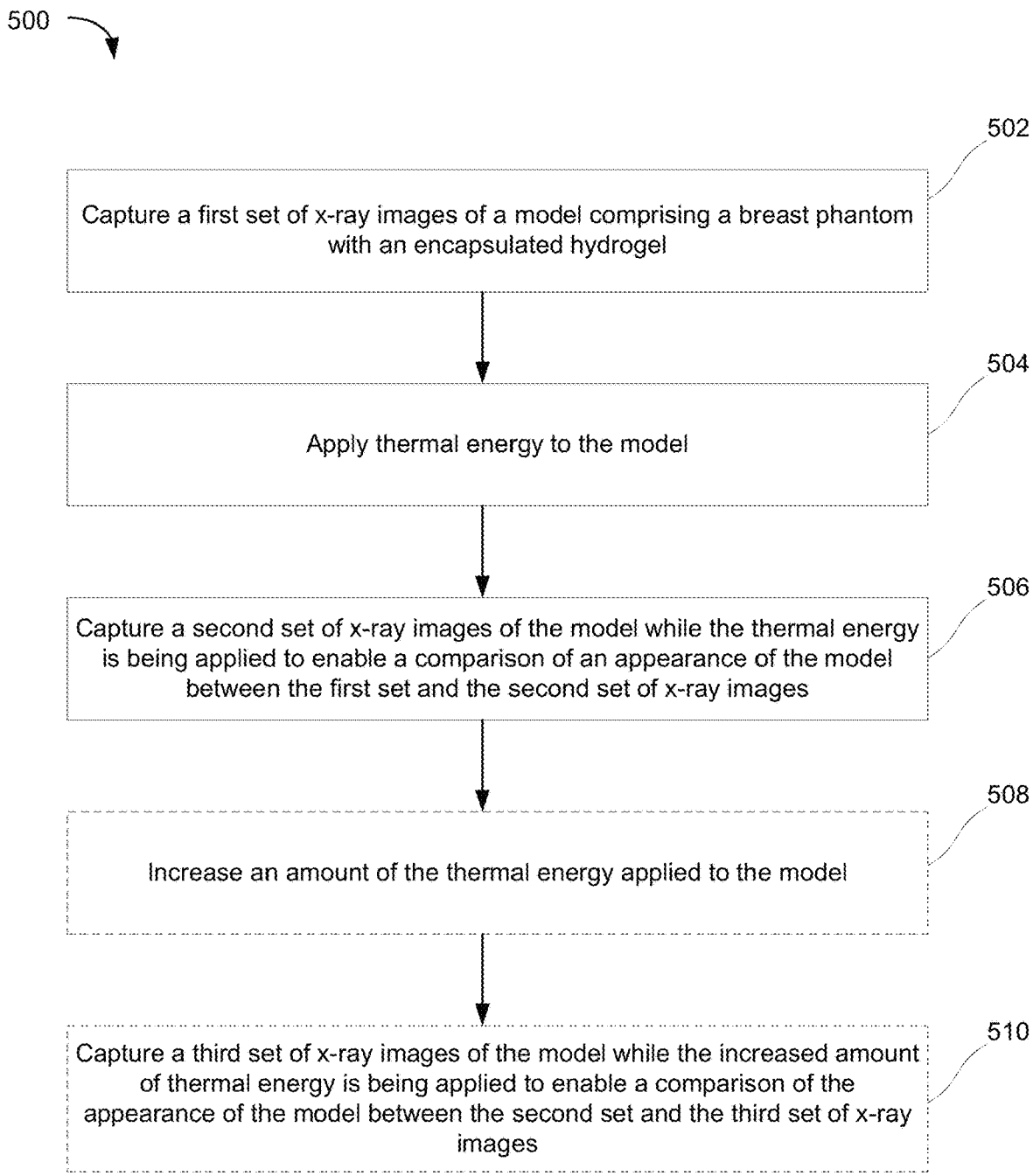
FIG. 5 depicts a method for testing effects of stimuli on breast appearance in an x-ray image.

FIG. 5 depicts a method 500 for testing effects of stimuli on breast appearance in an x-ray image. One example stimuli may include temperature (e.g., heat). At operation 502, a first set of x-ray images of a model 200 comprising a breast phantom 202 with an encapsulated hydrogel 204 may be captured using breast imaging system 100 described in detail with respect to FIGS. 1A and 1B. For example, once positioned on the support platform 106, the model 200 may be compressed and immobilized between the compression surfaces 110, 112 of the support platform 106 and the compression paddle 108, respectively, and the first set of x-ray images may be captured. At operation 502, no temperature may be applied to either of the compression surfaces 110, 112. Thus, the first set of x-ray images may serve as control x-ray images.

At operation 504, thermal energy may be applied to the model 200. For example, after the first set of x-ray images are captured at operation 502, the model 200 may be removed from the support platform 106 and heating system 134 may generate heat and increase the temperature of one or both of the compression surfaces 110, 112. The compression surfaces 110, 112 may be heated while the model 200 is removed to more realistically represent a clinical setting in which one or both of the compression surfaces 110, 112 would constantly remain heated to a particular temperature throughout the day. The model 200 may then be re-positioned on the support platform 106, and compressed between the compression surfaces 110, 112. The thermal energy may be transferred from one or both of the compression surfaces 110, 112 to the model 200 upon contact with the model 200. In one example, the temperature of one or both of the compression surfaces 110, 112 may be increased to about 30° C.

At operation 506, a second set of x-ray images of the model 200 may be captured using the breast imaging system 100 while the thermal energy is being applied. The first set of x-ray images and the second set of x-ray images may be compared to determine whether the increase in temperature affected an appearance of the model 200. In some examples, the determination may be made by a radiologist, or other similarly qualified specialist. In other examples, artificial intelligence may be employed for the determination. For example, the artificial intelligence may utilize image recognition techniques to determine differences in appearance.

At optional operation 508, an amount of thermal energy applied to the model 200 may be increased. For example, after the second set of x-ray images are captured at operation 506, the model 200 may be removed from the support platform 106 and the heating system 134 may increase the temperature of one or both of the compression surfaces 110, 112 from about 30° C. to about 35° C. In some examples, the amount of thermal energy may only be increased if it is determined that the appearance of the model 200 has not changed based on the comparison of the first and second set of x-ray images.

At optional operation 510, a third set of x-ray images of the model 200 may be captured using the breast imaging system 100 while the increased amount of thermal energy is being applied. The second set of x-ray images and the third set of x-ray images may be compared to determine whether the increase in temperature affected an appearance of the model 200.

Optional operations 508 and 510 may be repeated to incrementally increase the amount of the thermal energy applied and capture up to an $n^{th}$ set of x-ray images while the increased amounts of thermal energy are being applied. For example, the heating system 134 may incrementally increase the temperature of one or both compression surfaces 110, 112 from about 35° C. to about 40° C. and then from about 40° C. to 45° C. The range of temperatures applied to the compression surfaces 110, 112 (e.g., temperatures from about 30° C. to about 45° C.) are based on values deemed safe when contacting patient's skin. While the upper bound of the range from about 40° C. to 45° C. may be higher temperatures than what would be applied in an actual clinical setting, the full range may be tested to detect how breast appearance in x-ray images are affected by these higher temperatures in the event that there is slight fluctuation in temperature applied.

Table 1 provided below includes an example protocol for increasing the temperature of one or both compression surfaces 110, 112 of the breast support platform 106 (or breast tray) and compression paddle 108, respectively. In some examples, the optional operations 508 and 510 may be repeated until a determination is made that the appearance of the breast phantom 202 has changed in the most recently captured set of x-ray images.

TABLE 1

| | Temperature Applied (° C.) | | | |
| --- | --- | --- | --- | --- |
| | Parameter 1 | Parameter 2 | Parameter 3 | Parameter 4 |
| Breast Tray | 0 | 30 | 30 | 30 |
| Paddle | 0 | 0 | 30 | 33 |

From this testing process, an appropriate temperature range may be determined for heating the compression surfaces 110, 112 to reduce pain and discomfort for patients without compromising the quality of the x-ray image captured.

Figure 6:
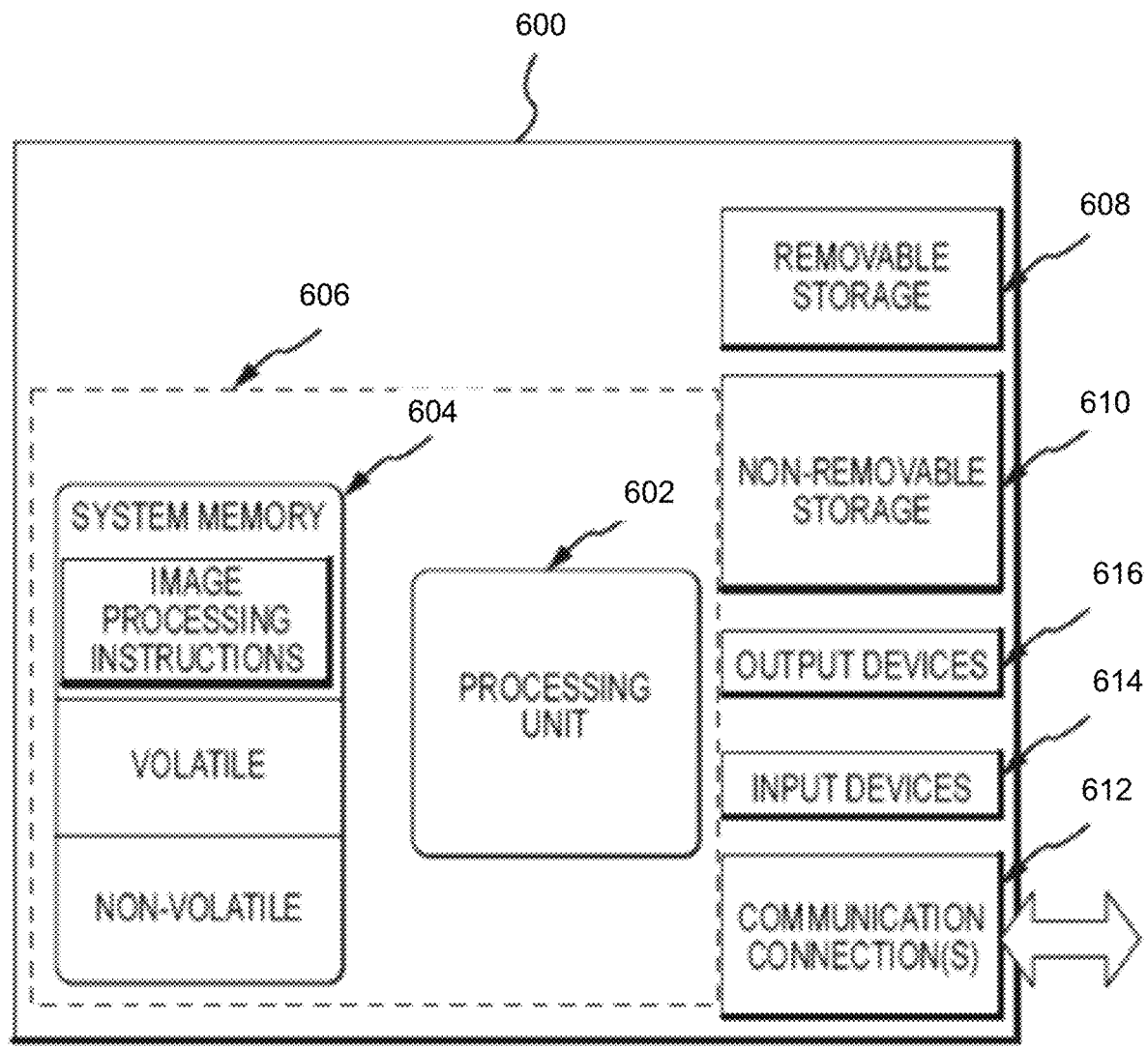
FIG. 6 illustrates one example of a suitable operating environment in which one or more of the present examples can be implemented.

FIG. 6 illustrates one example of a suitable operating environment 600 in which one or more of the present examples can be implemented. This operating environment may be incorporated directly into the imaging systems disclosed herein, or may be incorporated into a computer system discrete from, but used to control, the imaging systems described herein. This is only one example of a suitable operating environment and is not intended to suggest any limitation as to the scope of use or functionality. Other computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 600 typically includes at least one processing unit 602 and memory 604. Depending on the exact configuration and type of computing device, memory 604 (storing, among other things, instructions to perform the image acquisition and processing methods disclosed herein) can be volatile (such as RAM), non-volatile (such as ROM, flash memory, etc.), or some combination of the two. This most basic configuration is illustrated in FIG. 6 by dashed line 606. Further, environment 600 can also include storage devices (removable, 608, and/or non-removable, 610) including, but not limited to, magnetic or optical disks or tape. Similarly, environment 600 can also have input device(s) 614 such as touch screens, keyboard, mouse, pen, voice input, etc., and/or output device(s) 616 such as a display, speakers, printer, etc. Also included in the environment can be one or more communication connections 612, such as LAN, WAN, point to point, Bluetooth, RF, etc.

Operating environment 600 typically includes at least some form of computer readable media. Computer readable media can be any available media that can be accessed by processing unit 602 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 600 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some examples, the components described herein comprise such modules or instructions executable by a computer system that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some examples, computer system is part of a network that stores data in remote storage media for use by the computer system.

Figure 7:
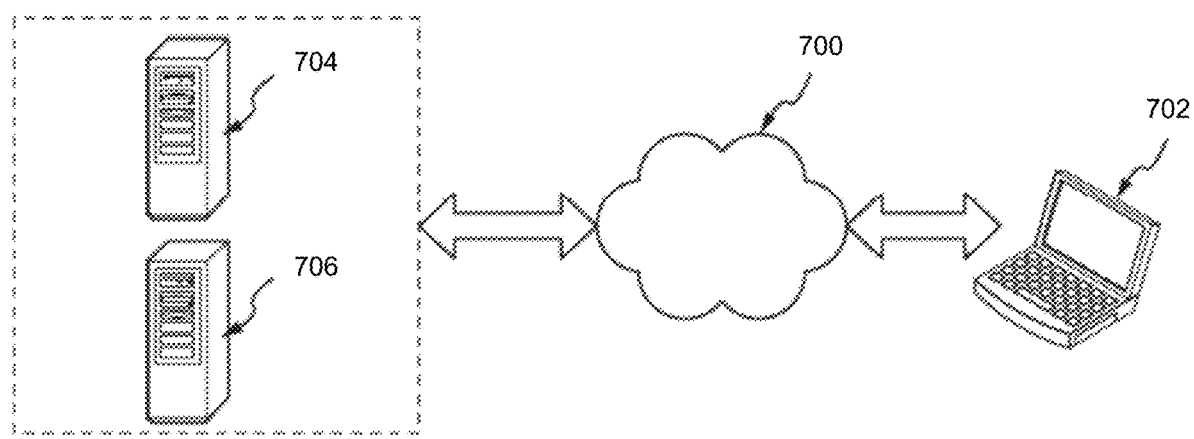
FIG. 7 is an example of a network in which the various systems and methods disclosed herein may operate.

FIG. 7 is an example of a network 700 in which the various systems and methods disclosed herein may operate. A client device, such as client device 702, may communicate with one or more servers, such as servers 704 and 706, via the network 700. In some examples, a client device may be a standalone device. The client device may also include or incorporate a laptop, a personal computer, a smart phone, a PDA, a netbook, or any other type of computing device, such as the computing device in FIG. 6. In some examples, servers 704 and 706 may also be any type of computing device, such as the computing device illustrated in FIG. 6. Network 700 may be any type of network capable of facilitating communications between the client device and one or more servers 704 and 706. For example, the surface image data and the internal image data may be acquired locally via the imaging systems and communicated to another computing device(s) for further processing, such as an image acquisition workstation or a cloud-based service. Examples of such networks include, but are not limited to, LANs, WANs, cellular networks, and/or the Internet.

In some examples, the various systems and methods disclosed herein may be performed by one or more server devices. For example, in one example, a single server, such as server 704 may be employed to perform the systems and methods disclosed herein, such as the methods for imaging discussed herein. Client device 702 may interact with server 704 via network 700. In further examples, the client device 702 may also perform functionality disclosed herein, such as scanning and image processing, which can then be provided to servers 704 and/or 706.

In alternate examples, the methods and systems disclosed herein may be performed using a distributed computing network, or a cloud network. In such examples, the methods and systems disclosed herein may be performed by two or more servers, such as servers 704 and 706. Although a particular network example is disclosed herein, one of skill in the art will appreciate that the systems and methods disclosed herein may be performed using other types of networks and/or network configurations.

In light of the foregoing, it should be appreciated that the present technology is able to provide an accurate model comprised of a breast phantom with encapsulated hydrogel for testing effects of stimuli, including heat, on breast appearance in x-ray images. For example, by incrementally applying thermal energy to the model and capturing x-ray images to determine appearance changes to the model as a result of the thermal energy, an appropriate temperature range may be determined for heating compression surfaces to reduce pain and discomfort for patients without compromising the quality of the x-ray image captured.

The examples described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some examples of the present technology with reference to the accompanying drawings, in which only some of the possible examples were shown. Other aspects may, however, be embodied in many different forms and should not be construed as limited to the examples set forth herein. Rather, these examples were provided so that this disclosure was thorough and complete and fully conveyed the scope of the possible examples to those skilled in the art. Further, as used herein and in the claims, the phrase "at least one of element A, element B, or element C" is intended to convey any of: element A, element B, element C, elements A and B, elements A and C, elements B and C, and elements A, B, and C.

Although specific examples are described herein, the scope of the technology is not limited to those specific examples. One skilled in the art will recognize other examples or improvements that are within the scope and spirit of the present technology. Therefore, the specific structure, acts, or media are disclosed only as illustrative examples. The scope of the technology is defined by the following claims and any equivalents therein.

What is claimed is:

1. A method comprising:
    capturing a first set of x-ray images of a model comprising a breast phantom with an encapsulated hydrogel;
    applying thermal energy to the model; and
    capturing a second set of x-ray images of the model while the thermal energy is being applied to enable a comparison of an appearance of the model between the first set and the second set of x-ray images.

2. The method of claim 1, wherein applying the thermal energy to the model comprises:
    applying the thermal energy to one or more of a first compression surface and a second compression surface of a breast imaging system; and
    compressing the model between the first compression surface and the second compression surface prior to and while capturing the second set of x-ray images, wherein contact of the model with the one or more of the first compression surface and the second compression surface transfers the thermal energy to the model.

3. The method of claim 2, wherein applying the thermal energy to one or more of the first compression surface and the second compression surface comprises:
    heating one or more of the first compression surface and the second compression surface to a temperature in a range of about 30° C. to about 45° C.

4. The method of claim 1, wherein a three-dimensional cell culture is encapsulated within the hydrogel to enable a comparison of an appearance of cells between the first set and the second set of x-ray images.

5. The method of claim 4, wherein the appearance of the cells are further analyzed using confocal microscopy.

6. The method of claim 1, wherein a plurality of channels corresponding to a vasculature of a breast are encapsulated within the hydrogel, and fluids are circulated within the plurality of channels while the first set and the set of x-ray images are being captured.

7. The method of claim 1, further comprising:
    increasing an amount of the thermal energy applied to the model; and capturing a third set of x-ray images of the model while the increased amount of thermal energy is being applied to enable a comparison of the appearance of the model between the second set and the third set of x-ray images.

8. An imaging system for imaging a model comprising a breast phantom with an encapsulated hydrogel, the system comprising:
   an x-ray source;
   an x-ray receptor;
   an immobilizer unit disposed between the x-ray source and the x-ray receptor, the immobilizer unit comprising a first surface and a second surface, wherein the model is disposed between the first surface and the second surface;
   a heating element disposed proximate at least one of the first surface and the second surface;
   a processor; and
   memory coupled to the processor and including instructions that, when executed by the processor, cause the system to perform a method comprising:
      capturing a first set of x-ray images of the model;
      applying thermal energy to the model by activating the heating element; and
      capturing a second set of x-ray images of the model while the thermal energy is being applied to enable a comparison of an appearance of the model between the first set and the second set of x-ray images.

9. The imaging system of claim 8, wherein applying the thermal energy to the model comprises:
   applying the thermal energy to one or more of the first surface and the second surface; and
   compressing the model between the first surface and the second surface prior to and while capturing the second set of x-ray images, wherein contact of the model with the one or more of the first surface and the second compression surface transfers the thermal energy to the model.

10. The imaging system of claim 9, wherein applying the thermal energy to one or more of the first surface and the second surface comprises:
   heating one or more of the first surface and the second surface to a temperature in a range of about 30° C. to about 45° C.

11. The imaging system of claim 8, wherein a three-dimensional cell culture is encapsulated within the hydrogel to enable a comparison of an appearance of cells between the first set and the second set of x-ray images.

12. The imaging system of claim 11, wherein the appearance of the cells are further analyzed using confocal microscopy.

13. The imaging system of claim 8, wherein the method further comprises circulating fluids within a plurality of channels corresponding to a vasculature of a breast and encapsulated within the hydrogel, while the first set and the set of x-ray images are being captured.

14. The imaging system of claim 8, wherein the method further comprises:
   increasing an amount of the thermal energy applied to the model; and
   capturing a third set of x-ray images of the model while the increased amount of thermal energy is being applied to enable a comparison of the appearance of the model between the second set and the third set of x-ray images.

* * * * *